US012127942B2

United States Patent
McPherson et al.

(10) Patent No.: US 12,127,942 B2
(45) Date of Patent: Oct. 29, 2024

(54) CUSTOMIZABLE AUGMENTS AND METHODS FOR ACETABULAR IMPLANTS

(71) Applicant: Zimmer, Inc., Warsaw, IN (US)

(72) Inventors: Edward J. McPherson, Warsaw, IN (US); Jacob Macke, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 659 days.

(21) Appl. No.: 15/984,996

(22) Filed: May 21, 2018

(65) Prior Publication Data

US 2018/0344465 A1    Dec. 6, 2018

Related U.S. Application Data

(60) Provisional application No. 62/512,904, filed on May 31, 2017.

(51) Int. Cl.
*A61F 2/30* (2006.01)
*A61F 2/34* (2006.01)

(52) U.S. Cl.
CPC ...... *A61F 2/30734* (2013.01); *A61F 2/30771* (2013.01); *A61F 2/34* (2013.01); *A61F 2002/30024* (2013.01); *A61F 2002/30131* (2013.01); *A61F 2002/30176* (2013.01); *A61F 2002/30181* (2013.01); *A61F 2002/30433* (2013.01); *A61F 2002/30449* (2013.01); *A61F 2002/30561* (2013.01); *A61F 2002/30578* (2013.01); *A61F 2002/30617* (2013.01); *A61F 2002/30688* (2013.01);
(Continued)

(58) Field of Classification Search
CPC ..... A61F 2/34; A61F 2/30734; A61F 2/30771
See application file for complete search history.

(56) References Cited

U.S. PATENT DOCUMENTS

| 5,282,861 A | 2/1994 | Kaplan | |
|---|---|---|---|
| 2018/0036129 A1* | 2/2018 | Mistry | ..................... A61F 2/34 |
| 2018/0161163 A1* | 6/2018 | Macke | ................ A61F 2/30744 |

FOREIGN PATENT DOCUMENTS

| EP | 3409241 | 9/2023 |
|---|---|---|
| FR | 2960418 | 12/2011 |

(Continued)

OTHER PUBLICATIONS

"European Application Serial No. 18175381.5, Response filed Apr. 3, 2020 to Communication Pursuant to Article 94(3) EPC Sep. 23, 2019", 13 pgs.

(Continued)

*Primary Examiner* — Jerrah Edwards
*Assistant Examiner* — Christine L Nelson
(74) *Attorney, Agent, or Firm* — Schwegman Lundberg & Woessner, P.A.

(57) ABSTRACT

An augment for supporting an acetabular shell at an acetabulum of a hip bone. In some examples, the augment can include a body having a first surface and a second surface opposite the first surface. The body can extend from a first end portion that is adapted to be fixed to an acetabular shell, to a second end portion. The body can include a first hole and a second hole, each of the first and second holes extending through the body from the first surface to the second surface. The body can be formed of a porous material that promotes boney ingrowth and can further include a trim marker located in between the first hole and the second hole.

17 Claims, 7 Drawing Sheets

(52) U.S. Cl.
CPC .......... *A61F 2002/3069* (2013.01); *A61F 2002/30736* (2013.01); *A61F 2/30749* (2013.01); *A61F 2002/30784* (2013.01); *A61F 2002/3092* (2013.01); *A61F 2002/3093* (2013.01); *A61F 2/30942* (2013.01); *A61F 2002/3096* (2013.01); *A61F 2002/30968* (2013.01); *A61F 2002/3097* (2013.01); *A61F 2002/30985* (2013.01); *A61F 2310/00023* (2013.01)

(56) References Cited

FOREIGN PATENT DOCUMENTS

| WO | WO2011156504 | * | 8/2011 | ............ A61F 2/30 |
|----|--------------|---|--------|------------------------|
| WO | 2015187038   |   | 12/2015 |                       |
| WO | 2017005514   |   | 1/2017  |                       |

OTHER PUBLICATIONS

"European Application Serial No. 18175381.5, Extended European Search Report mailed Oct. 31, 2018", 8 pgs.

"European Application Serial No. 18175381.5, Response filed Jun. 5, 2019 to Extended European Search Report mailed Oct. 31, 2018", 17 pages.

"European Application Serial No. 18175381.5, Communication Pursuant to Article 94(3) EPC Sep. 23, 2019", 5 pages.

Levine, Brett R, et al., "Experimental and clinical performance of porous tantalum in orthopedic surgery", Biomaterials, (27), (Sep. 2006), 4671-81.

"European Application Serial No. 18175381.5, Communication Pursuant to Article 94(3) EPC mailed Oct. 27, 2020", 5 pgs.

"European Application Serial No. 18175381.5, Response filed Mar. 8, 2021 to Communication Pursuant to Article 94(3) EPC mailed Oct. 27, 2020", 14 pages.

* cited by examiner

CUSTOMIZABLE AUGMENTS AND METHODS FOR ACETABULAR IMPLANTS

CLAIM OF PRIORITY

This application claims the benefit of U.S. Provisional Patent Application Ser. No. 62/512,904, filed on May 31, 2017, the benefit of priority of which is claimed hereby, and which is incorporated by reference herein in its entirety.

TECHNICAL FIELD

This document pertains generally, but not by way of limitation, to orthopedic devices, and, more particularly, to augments that support acetabular implants used in total hip arthroplasty.

BACKGROUND

A total hip arthroplasty (THA) procedure can be performed to repair a diseased or damaged hip joint and replace it with a hip prosthesis. Sometimes, as with any other mechanical device, a total hip replacement can be subject to various forms of mechanical or biological issues. When issues occur, a reoperation of the hip prosthesis can be necessary to resolve the issues. Such a reoperation of a THA is called a revision THA. This is usually done several years after the original implantation and is more common in patients who had the initial THA performed at a young age and the patient chose to have a very active physical lifestyle.

One of the challenges of a THA, including a revision THA is how to securely implant the hip prosthesis. In particular, it can be challenging to securely implant an acetabular shell of the prosthesis into the remaining bone of the patient, especially in the presence of poor bone quality or bone loss.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

As discussed above, one of the challenges of a total hip arthroplasty (THA), including a revision THA, is how to securely implant the hip prosthesis. In particular it can be difficult to implant an acetabular revision shell of the prosthesis into the remaining bone of the patient, especially in the presence of poor bone quality or bone loss.

When using conventional acetabular revision shells, surgeons can employ the use of additional augments to reinforce the attachment of the shell to the bone. Additional components can include a cup-cage construct. Cup-cage constructs can be used when the surgeon determines there is a risk of the cup migrating or loosening. The cage holds the cup in place long enough to provide biological fixation to the acetabular cup. However, the cup-cage construct reduces an allowable head size that can be placed in the shell.

In addition, surgeons are limited to off the shelf options having specified dimensions. These off the shelf augments limit the surgeon's ability to match the implant to the specific needs and dimensions of the patient. The surgeon, selecting from these off the shelf options, is limited in finding a best match for fixing the shell to the available bone. When the augments are too large or too small and the surgeon tries to match the augments up with the available bone, it does not always produce the desired results. Too small of an augment may not provide the desired fixation of the implant to the bone, while too large of an augment may interfere with the patient's anatomy adjacent the implant site.

The other option available to surgeons is to have a patient specific, fully customized implant manufactured. This option also has issues. Fully customized implants are not readily available off the shelf. They are manufactured to match a particular patient based on imaging data for the particular patient.

To address these issues, improved augments and methods for supporting acetabular shells are described herein. The augments and methods can include modification options to increase the customizability of the augments to better match the anatomy of a patient. The augments have been found by the inventors to solve the problem of providing sufficient screw fixation in revision total hip arthroplasty (THA) when many fasteners can be required to achieve biological fixation of the shell, while providing the ability to eliminate unnecessary portions of the augment. The augments and methods can allow tailored fixation of the augment to the particular patient. In other words, the improved augments can provide individualized customization to the particular patient's anatomy in an "off the shelf" design. The advantages of the improved augments can include: providing flexibility to the surgeon for selecting implant sizes that match the native bone, as well as preserving a maximized head size within the cup because the use of a cage can be eliminated.

The augments and methods disclosed herein can improve surgeon options for attaching acetabular shells to an acetabulum of patient in a more customizable manner, and without the expense of a fully customized, patient-specific implant. Because the augments are more customizable to the patient over conventional augments, the quality of the implantation can be made more reliable.

Another feature of an improved augment can include having a smooth surface on specified portions of the augment, and having a porous surface that promotes boney ingrowth on other specified portions of the augment. The advantages of such a surface arrangement can include facilitating improved attachment to the bone along the porous surface portions, while the smooth surface portions can be arranged to reduce irritation of adjacent tissue, including adjacent muscle tissue that covers the hip bone.

The disclosure herein while applied to implanting shells, can also be applied to implanting cups, such as a cup inserted into a shell that acts as a liner, or a cup directly implanted without a shell. In addition, while the augments and methods can be described in relation to revision THA, the augments and methods can also be applied to non-revision, or first time THA surgeries and prosthesis.

As described herein, the term "hole" is generally associated with a screw hole, but it is not limited to holes that can only be used with screws. Other suitable types of fasteners besides screws can be inserted through the holes disclosed herein.

Figure 1A:
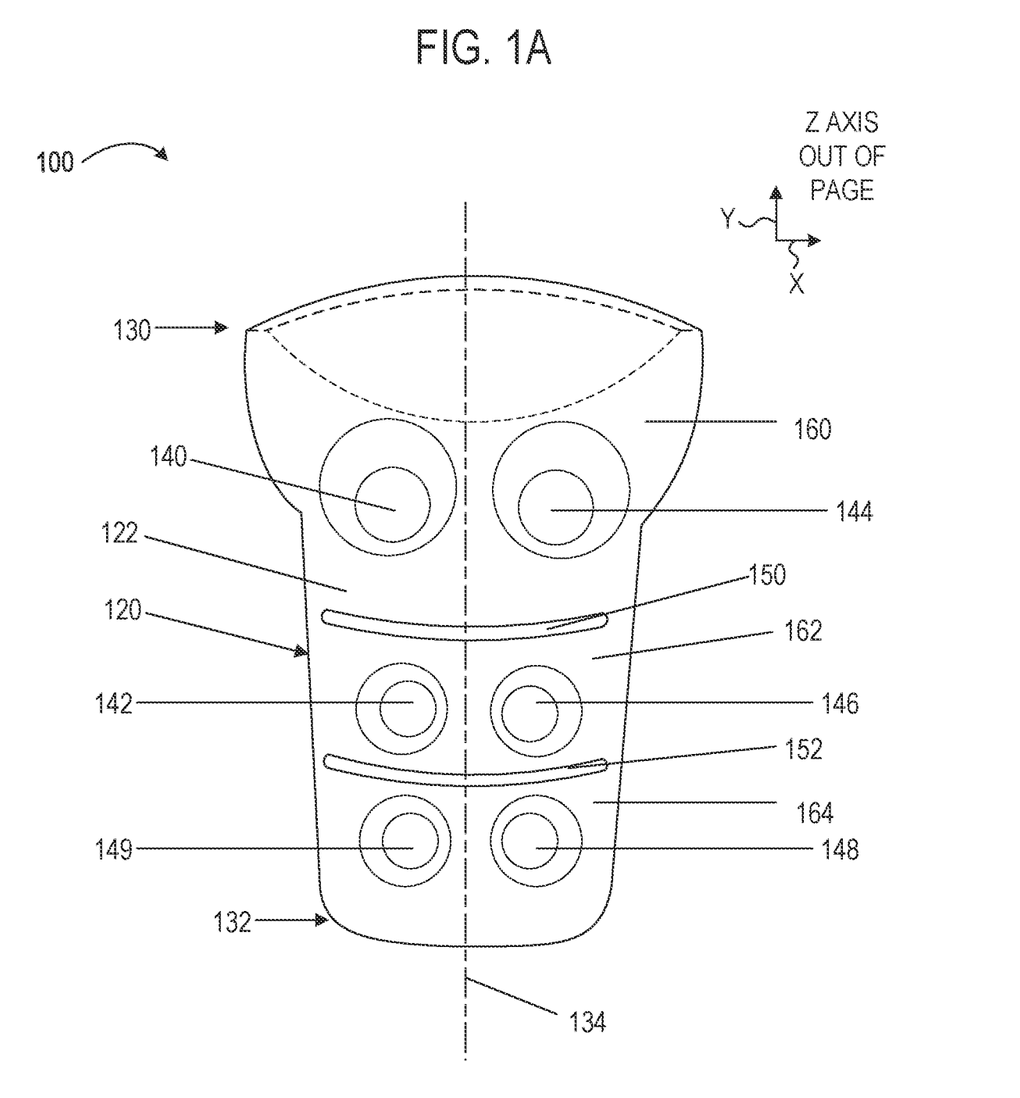
FIG. 1A is a top view of an illustrative augment, in accordance with at least one example.
Figure 1B:
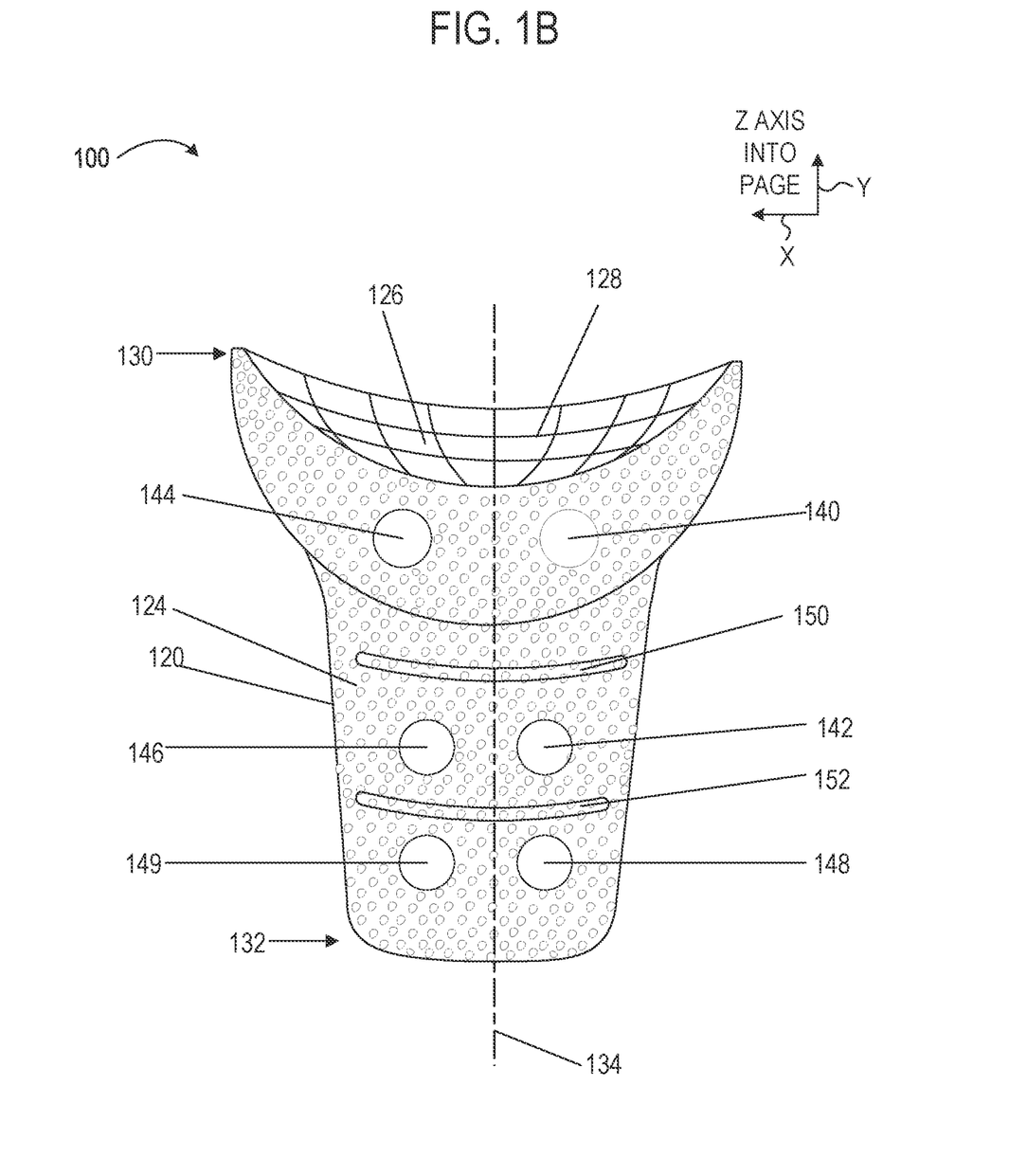
FIG. 1B is a bottom view of the illustrative augment of FIG. 1A, in accordance with at least one example.
Figure 1C:
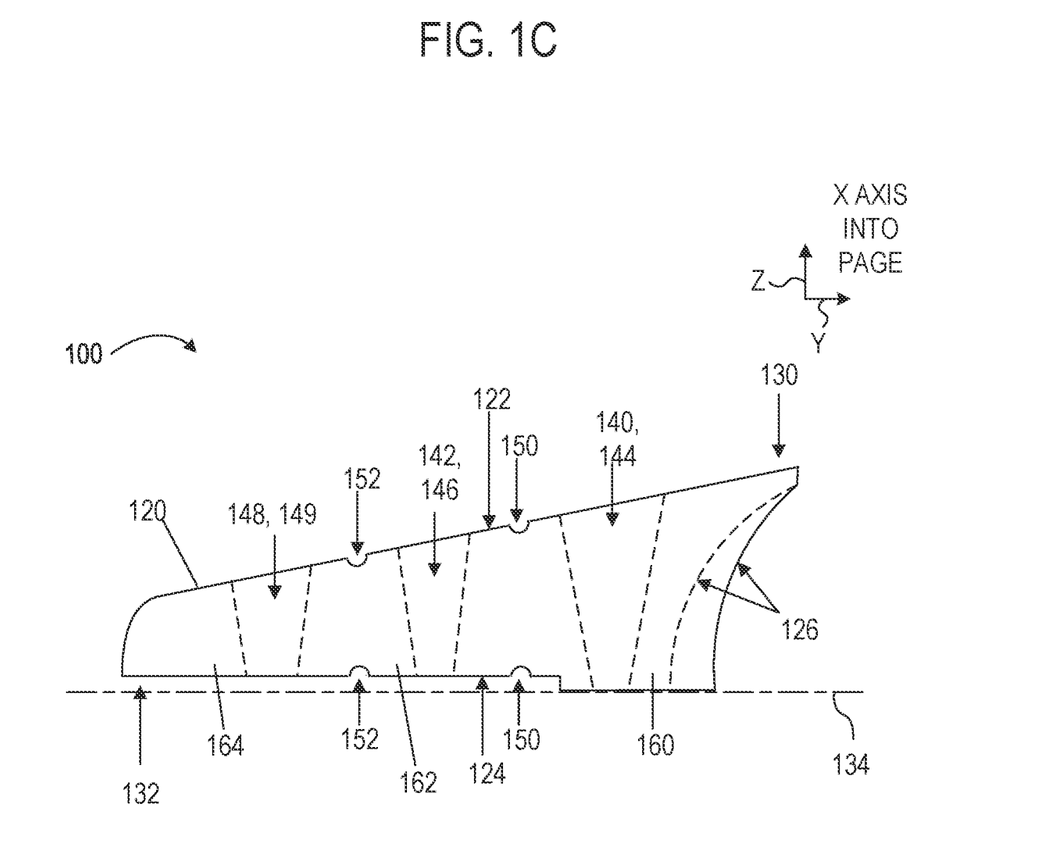
FIG. 1C is a side view of the illustrative augment of FIG. 1A, in accordance with at least one example.

FIGS. 1A, 1B and 1C are top, bottom and side views of an illustrative augment for supporting an acetabular shell at a bone, in accordance with at least one example. As a general overview, the example augment of FIGS. 1A, 1B and 1C can include removable portions to allow customization of the augment to fit a particular patient's anatomy.

The augment 100 can include a body 120 having a first surface 122 and a second surface 124 (FIG. 1B) opposite the first surface 122. The body 120 can extend from a first end portion 130 to a second end portion 132. In some examples the body 120 can be described as extending along a longitudinal axis 134 from the first end portion 130 to the second end portion 132. The provision of the longitudinal axis 134 does not necessarily mean that the augment 100 extends symmetrically along the longitudinal axis 134 or is aligned with the longitudinal axis 134, although in some examples, it could be. Rather, the longitudinal axis 134 is provided as a general directional relationship of the augment 100 to itself and to an acetabular shell. Furthermore, any other features that are described as extending along the longitudinal axis 134 are also not necessarily aligned with, parallel or symmetric about the longitudinal axis, although in some examples, some features can be.

Figure 2A:
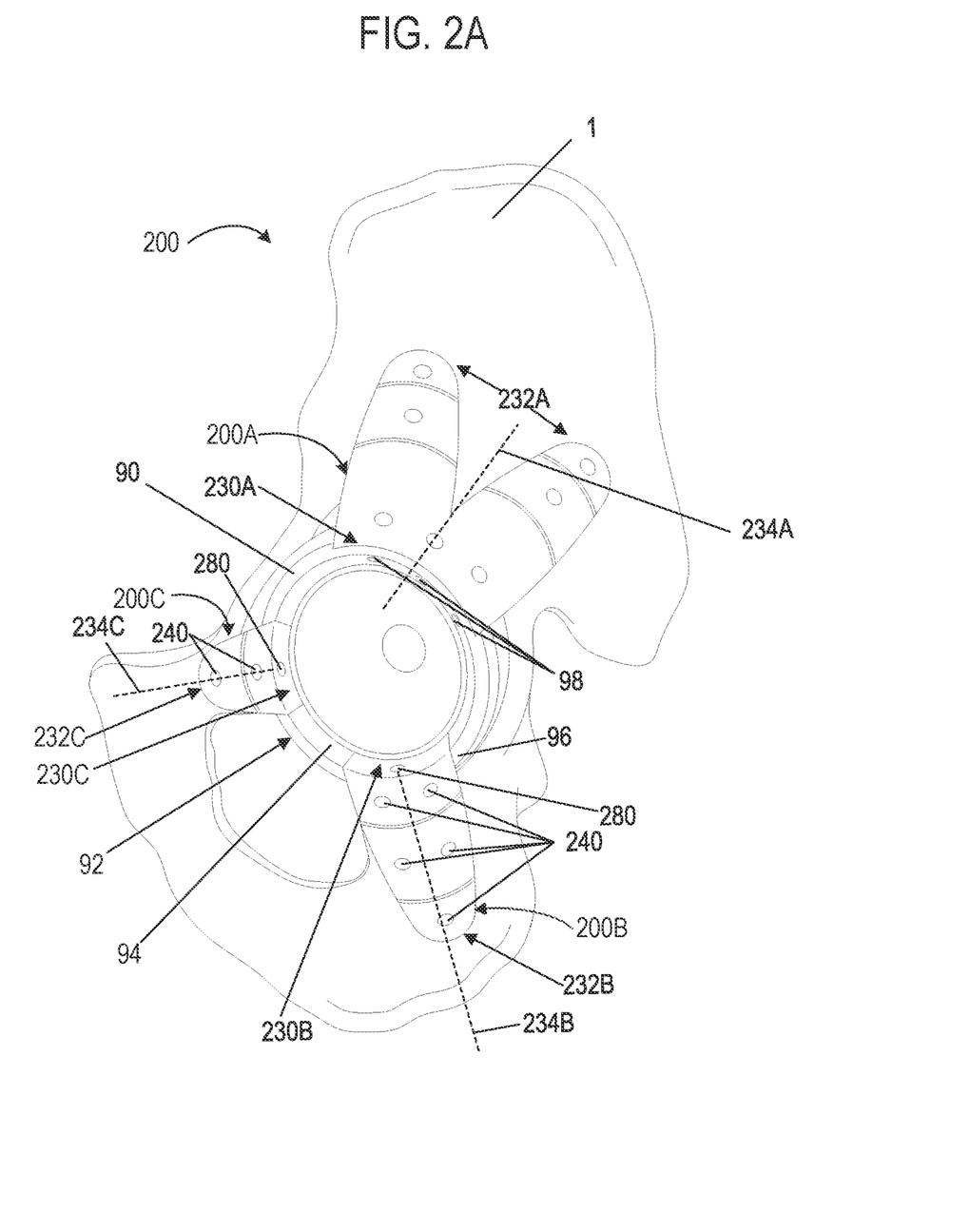
FIG. 2A is a perspective view of illustrative augments arranged around an acetabular shell at a hip bone, in accordance with at least one example.

The first end portion 130 of the augment 100 can be adapted to be fixed to an acetabular shell 90, hereinafter shell 90, such as the shell 90 shown in FIG. 2A. For example, with reference to FIGS. 1B, 1C, and 2A, the first end portion 130 of the augment 100 can include a third surface 126 that is shaped to conform to an exterior surface 92 of the shell 90. With further reference to FIGS. 1B, 1C, and 2A, the third surface 126 can be a curved surface that can be shaped to conform to the shell 90, such as a generally spherical surface portion of the shell 90. The third surface 126 represents merely one example shape that can be used. Any suitable shape for mating the third surface 126 with an exterior surface (e.g., 92 of FIG. 2A) of any acetabular shell can be used. The first end portion 130 can be adapted to be cemented to and/or screwed to the exterior surface 92 of the shell 90. Any other suitable fastening method can also be used.

In some examples, the third surface 126 can include gripping formations 128 (FIG. 1B) to promote adhesion of the third surface 126 and the shell 90, such as when an augment 100 is cemented to the exterior surface 92 of the shell 90. In some examples where the third surface 126 includes the gripping formations 128, the third surface 126 may not include the porous material that promotes boney ingrowth, or the third surface 126 can be less porous than the second surface 124.

To fasten the augment 100 to bone, the augment 100 can include a first hole 140 and a second hole 142. Each of the first and second holes 140, 142 can extend through the body 120 of the augment 100 from the first surface 122 to the second surface 124. In some examples, and as shown in FIGS. 1A-1C, the first and second holes 140, 142 can be described as being arranged along the longitudinal axis 134. In some examples, the first and second holes 140, 142 can be arranged serially (e.g., in series, spaced apart, one after the other) along the longitudinal axis 134. While the first and second holes 140, 142 can be described as extending along the longitudinal axis 134, this does not mean that all of the various holes described herein are necessarily symmetric about, aligned to, or aligned parallel to the longitudinal axis 134, or even aligned with one another. The longitudinal axis 134 merely provides a general directional relationship of the holes with respect to each other and location along the augment and in relation to the shell it supports. However, in some examples, any of the various holes or other features can be aligned to or symmetric about the longitudinal axis 134.

To facilitate improved customization of the augment 100 to a patient, a trim marker 150 indicating a trim location can be provided on the augment 100. The trim marker 150 can be located, for example, in between the first hole 140 and the second hole 142. The trim marker 150 can indicate a location on the body 120 of the augment 100 where a portion (e.g. predetermined portion) of the augment 100 can be removed in order to reduce the size of the augment when the entire augment is not needed for a particular patient. Reasons the surgeon would reduce the size of the augment can include: the augment 100 is larger than needed, or the patient has a lack of good bone to fasten to in that portion of the augment 100. Reducing the size of the augment 100 to only what is needed in the particular patient provides the surgeon the ability to optimize the fit of the augment to the host bone. In addition to the fit being optimized, the need to remove additional host bone in order to achieve a natural implant positioning and orientation can be reduced. Achieving proper positioning of the shell can lead to improved hip kinematics in the patient.

In some examples, the trim marker 150 can indicate a location on the body 120 that is more frangible than other portions of the body 120. In particular, the trim marker 150 can indicate a location that is more frangible than the portions adjacent to (e.g., the portions next to, or directly adjacent to) the trim marker 150. For example, the trim marker 150 can be located in between a first portion 160 of the augment and a second portion 162 of the augment (FIGS. 1A and 1C). The first portion 160 can include the first hole 140, and the second portion 162 can include the second hole 142. The trim marker 150 can be sandwiched between the first portion 160 and the second portion 162, and the trim marker 150 can include characteristics that make the body 120 more easily fracturable at the trim marker 150 than the portion of the first portion 160 and the second portion 162 that are directly adjacent to the trim marker 150.

As perhaps best shown in FIG. 1C, the augment 100 can have a thickness from the first surface 122 to the second surface 124, such as the thickness defined along the Z-axis. The thickness can be relatively constant, or, as shown in FIG. 1C, the thickness can vary, such as along the longitudinal axis 134.

To facilitate fracture, the trim marker 150 can be a region of the body 120 having a decreased thickness of the body 120. The thickness in the area of the trim marker 150 can be thinner than the first and second portions 160, 162, it can be thinner than the portion of the first and second portions 160, 162 directly adjacent to the trim marker 150, or, it can be thinner than the majority of the body 120. Other examples of mechanisms that facilitate fracturability at the trim marker (e.g., 150) can include: different material characteristics, porosity, compositions or geometry at the trim marker compared to other portions of the body 120. Geometric features can also include perforations through the thickness of the body 120 at the trim marker, or specific crack propagation features that are not loaded under normal use, but that can be intentionally activated to initiate fracture by the surgeon.

Figure 1D:
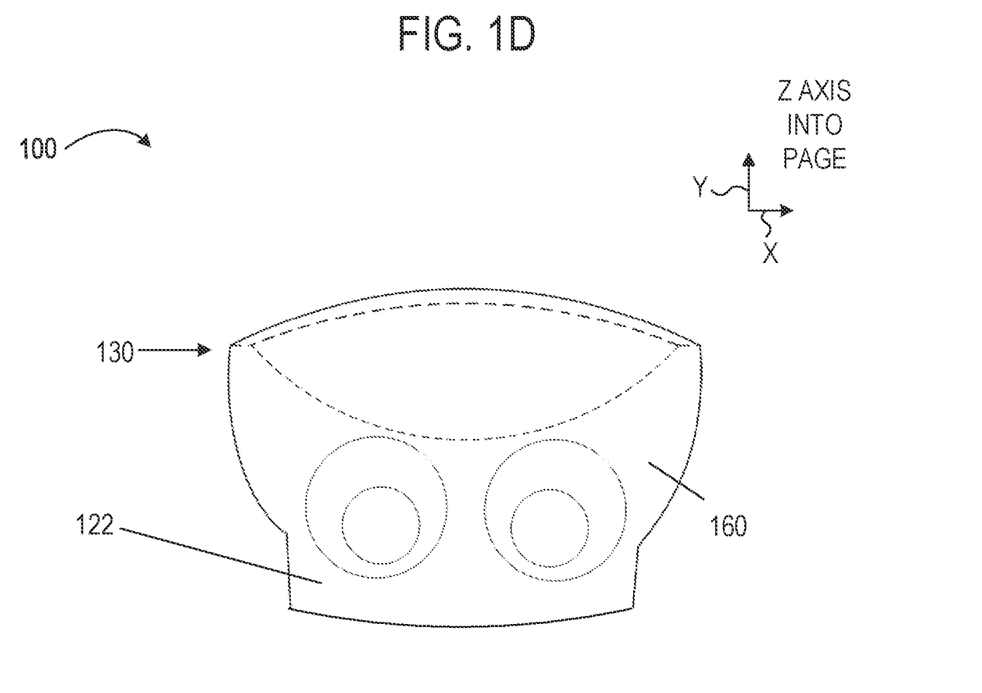
FIG. 1D is a top view of the illustrative augment of FIG. 1A, with a portion of the augment from a trim marker to a second end portion removed.

Another feature shown in FIGS. 1A-1C that can be included in some example augments 100 is a third hole 144 and/or a fourth hole 146. Like the first and second holes 140, 142, each of the third and fourth holes 144, 146 can extend through the body 120 from the first surface 122 to the second surface 124. Also like the first and second holes 140, 142, the third and fourth holes 144, 146 can be described as being arranged along the longitudinal axis 134. In some examples, the trim marker 150 can be located in between the third hole 144 and the fourth hole 146. In such an example, the first hole 140 and the third hole 144 can be located on the first 160 portion of the body 120, and the second hole 142 and the fourth hole 146 can be located on the second portion 162 of the body 120. This arrangement can allow the second hole 142 and the fourth hole 146 to be removed at the trim marker 150 if the second portion 162 is not needed or wanted by the surgeon to support the shell 90 (e.g., FIG. 2A). FIG. 1D shows the augment 100 of FIG. 1A with the portion of the body 120 from the trim marker 150 to the second end portion 132 removed.

As shown in FIGS. 1A-1C, in some examples the augment can include a fifth hole 148 and a sixth hole 149. The fifth hole 148 and the sixth hole 149 can be arranged on a third portion 164 (FIGS. 1A, 1C) of the augment 100. The third portion 164 can be separated from the second hole 142 and the fourth hole 146 by a second trim marker 152. The second trim marker 152 can indicate a second trim location representing a portion (e.g., predetermined portion) of the augment 100 that can be removed. The second trim marker 152 can include any of the features previously described with respect to the trim marker 150.

In some examples the second trim marker 152 can be provided without the presence of the "first" trim marker 150. In other words, the fifth and sixth holes 148, 149 can be optionally removable, while none of the first, second, third or fourth holes 140, 142, 144, 146 are intended for removal. For example, during the design process it could be determined that a minimum arrangement of holes in a particular augment is needed for sufficient attachment to the hip bone that is different from the particular embodiment disclosed herein, and only the trim markers that correspond to acceptably removable portions of the augment are provided in a particular design.

While the trim markers 150, 152 described herein are depicted as generally perpendicular to the longitudinal axis 134, the trim markers can extend in any suitable direction and location depending on the application.

The features of the augments described herein can be incorporated into different types of augments and in different forms. As shown in the example of FIGS. 1A-1C, the augment can be a buttress-type augment. For example, in the buttress augment of FIGS. 1A-1C, the body 120 can be adapted to structurally support an acetabular shell (e.g., 90, FIGS. 2A-2B) that is implanted in a patient having a Paprosky type IIIA defect. Example buttress augments can include structural augments to address Paprosky Type IIIA defects including superior segmental defects, cavitary defects, or both, among others. The example buttress augment can beneficially accomplish this in more patients, without fully custom patient-matched implants or bulk allografts.

In some examples, and as previously described, the augment 100 can include a porous material that promotes boney ingrowth (e.g., supports boney ingrowth). In some examples, the augment 100 can be made partly or entirely of the porous material, partly or entirely of a solid material that is generally non-porous (e.g., solid metal, solid polymeric material), or a combination of both solid and porous materials.

In the example of FIGS. 1A-1C, the first surface 122 can include a smooth, generally non-porous surface (e.g., most or all of the first surface can be a smooth, non-porous surface) and can be adapted to face away from the bone surface when implanted. One benefit of the first surface 122 being smooth can be that it allows the first surface 122 not to irritate the tissues, including muscle tissue that is adjacent the augment 100 and covering the bone.

In contrast to the smooth, generally non-porous first surface 122, the second surface 124 can be adapted to mate with the bone surface when implanted and can include the porous material that promotes boney ingrowth. One benefit of having the second surface 124 being porous material can be that it promotes boney ingrowth for better fixation to the bone. Boney ingrowth into the porous material can provide a stronger structural connection to the bone as the bone grows into the porous material over time.

Another benefit of the porous material at the second surface 124 can be that the porous surface exhibits a high coefficient of friction against the bone which can provide enhanced stability. In the example of FIGS. 1A-1C, the first surface 122 can have a first coefficient of friction, and the second surface 124 can have a second coefficient of friction. The first coefficient of friction can be less than the second coefficient of friction. This arrangement can improve the grip between the bone and the second surface 124 of the augment 100, while allowing the muscle tissue over the hip bone to glide over the first surface 122 of the augment 100.

To facilitate boney ingrowth, any of the augments described herein can be formed of a three-dimensional structure that promotes (e.g., supports) boney ingrowth. For example, a highly porous, three-dimensional metallic structure can be provided that incorporates one or more of a variety of biocompatible metals such as but not limited to titanium, a titanium alloy, cobalt chromium, cobalt chromium molybdenum, tantalum, a tantalum alloy, niobium, or alloys of tantalum and niobium with one another or with other metals. Such structures are particularly suited for contacting bone and/or soft tissue, and in this regard, can be useful as bone substitutes and other implants and implant components that are receptive to cell and tissue ingrowth, for example, by allowing boney tissue or other tissue to grow into the porous structure over time to enhance fixation (e.g., osseointegration) between the structure and surrounding bodily structures. According to certain examples of the present disclosure, an open porous metal structure, or a portion thereof, can have a bulk porosity as low as 55%, 65%, or 75% or as high as 80%, 85%, or 90%, or within any range defined between any pair of the foregoing values, and in this regard, such structures can provide lightweight, yet strong porous implants. Certain porous metal structures, despite having such high porosities, are capable of withstanding extreme mechanical loads at the time of implantation and over long periods of time, for example, where a highly porous, three-dimensional metallic structure is forcefully impacted and press fit into a bone, by itself or connected to another implant, and maintains its shape during impaction and following many months or years of service in the body. Such structures can be manufactured according to any suitable technique or process. An example of an open porous metal structure is produced using Trabecular Metal™ Technology available from Zimmer, Inc., of Warsaw, Indiana. Trabecular Metal™ is a trademark of Zimmer, Inc. Such a material can be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

In some instances, a highly porous, three-dimensional metallic structure will be fabricated using a selective laser sintering (SLS) or other additive manufacturing-type process such as direct metal laser sintering or electron beam melting. In one example, a three-dimensional porous article is produced in layer-wise fashion from a laser-fusible powder, e.g., a single-component metal powder, which is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain examples, a laser selectively fuses powdered material by scanning cross-sections generated from a 3-D digital description of the article, e.g., from a CAD file or scan data, on the surface of a powder bed. Complex geometries can be created using such techniques, and in some instances, net shape and near net shape implants are constructed. In some examples, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as any of those disclosed herein.

Generally, a highly porous, three-dimensional metallic structure will include a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate can be in direct contact with the ligaments of the highly porous structure, for example, approximately 15%, 20%, or 25%, of the surface area of the substrate can be in direct contact with the ligaments of the highly porous structure.

A highly porous, three-dimensional metallic structure can be fabricated such that it comprises a variety of densities in order to selectively tailor the structure for particular orthopedic applications, for example, by matching the structure to surrounding natural tissue in order to provide an improved matrix for tissue ingrowth and mineralization. Such structures can be isotropic or anisotropic. In this regard, according to certain examples, an open porous metal structure can be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure can have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

In some examples, the porous metal structure can be a formed from a titanium alloy using an additive manufacturing process, such as with OsseoTi™, which is commercially available from Biomet Manufacturing, LLC (Warsaw, Ind., USA). Briefly, however, OsseoTi™ is highly biocompatible, has high corrosion resistance and includes a highly interconnected porous architecture that mimics the porous structure of human cancellous bone, which can enhance bone integration and in-growth. In one exemplary implementation, OsseoTi™ can include a porous construct with a porosity.

Figure 2B:
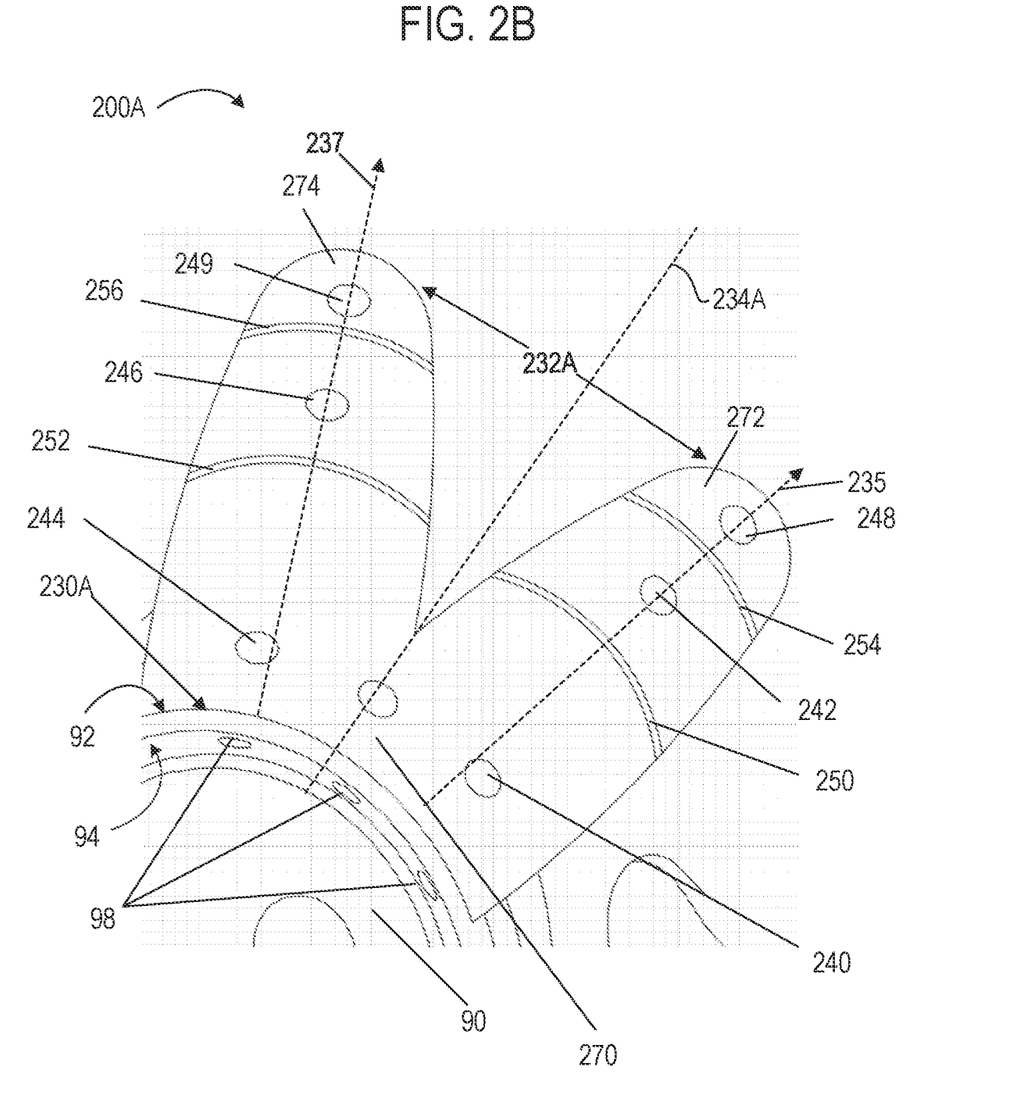
FIG. 2B is a close up perspective view of one of the illustrative augments of FIG. 2A, in accordance with at least one example.

FIG. 2A is a perspective view of illustrative augments 200A, 200B, 200C arranged around an acetabular shell 90 at a hip bone 1, in accordance with at least one example. FIG. 2B is a close-up perspective view of the illustrative augment 200A of FIG. 2A.

As shown in FIG. 2A, the acetabular shell 90 can be arranged at an acetabulum of the hip bone and one or more of the augments 200A, 200B, 200C can be arranged around the shell 90 to support the shell 90. These augments can be particularly useful when there is lost or missing bone, as can be the case when a patient has Paprosky type IIIA defects. However, the illustrative augments 200A, 200B, 200C can also be used to address other issues and defects, and the features described herein can be used with other augments that are not related to addressing Paprosky rated defects.

The example of FIG. 2A depicts a system 200 having three augments including a first augment 200A, a second augment 200B, and a third augment 200C. The first augment 200A can be generally described as a buttress augment. The second and third augments 200B, 200C can be generally described as L-brackets. Three augments are shown in the system 200, but any suitable number of augments can be used. In some examples, a single augment can be used, or any of the augments can be used in combination with other augments different than the augments shown and described herein.

Any of the features shown and described with reference to the augment 100 of FIGS. 1A-1D, can be incorporated into any of the first, second and third augments 200A, 200B and 200C (e.g., the augments) of FIGS. 2A and 2B. Like the augment 100 of FIGS. 1A-1C, and with reference to element numbers of FIGS. 1A-1C, each of the augments 200A, 200B and 200C can include a body (e.g., 120) having a first surface (e.g., 122) adapted to face away from the bone 1 and a second surface (e.g., 124) opposite the first surface (e.g., 122) adapted to face the bone 1.

The body of each of the augments 200A, 200B and 200C can extend from respective first end portion 230A, 230B, 230C proximal to the shell, to respective second end portion 232A, 232B, 232C distal from the shell. Each of the augments 200A, 200B and 200C can extend along respective longitudinal axes 234A, 234B, 234C in the manner described previously with regard to the longitudinal axis 134 of FIGS. 1A-1C.

Referring back to FIG. 2A, the first end portions 230A, 230B and 230C of each of the augments 200A, 200B and 200C can be adapted to be fixed to the acetabular shell 90 (FIG. 2A). In some examples, the first end portions 230A, 230B, 230C can be adapted to be cemented to and/or screwed to the acetabular shell 90, however, any suitable fastening method can be used to fasten the augments to the shell 90. In some examples, such as shown in the example of the first augment 200A, while not required, it can be preferable for the first augment 200A to be placed proximate the acetabular shell 90 at the exterior surface 92 of the acetabular shell 90. In some examples, it can be preferable for the first end portion 230A to be directly attached to the exterior surface 92 of the shell 90 by bone cement. In addition to bone cement, as shown in FIG. 2B, the shell 90 can be fastened to the first augment 200A via fasteners inserted through shell holes 98 that can screw into augment 200A, and optionally, the bone 1.

In other augment examples, such as is shown for the second and third augments 200B and 200C in FIG. 2A, it can be preferable for the augments 200B, 200C to include a flange or clip at the first end portions 230B, 230C that extends over a rim 96 of the shell 90 and attaches to an interior surface 94 of the shell 90. The attachment of the second and third augments 200B, 200C to the shell 90 can be made at attachment holes 280 on the flange. In some examples, the flange or clip at the first end portion can attach to the exterior surface 92 of the shell 90 instead of the interior surface 94, or in addition to the interior surface 94. In some examples, attachment holes 280 can be omitted and other fastening features may be provided, or other fastening features can be provided in addition to attachment holes 280. One such method of fastening can include an augment and a shell having interlocking geometry that restricts movement between the augment and shell.

In some examples any of the augments 200A, 200B, 200C can be implanted using a cancellous screw fastened through both the shell 90 and the respective augment 200A, 200B, 200C. In some examples, the cancellous screw can also extend into the bone. In some examples, any of the augments 200A, 200B, 200C can be fastened to the shell 90 using a machine screw. More than one method of fastening may be used.

The second and third augments 200B, 200C can include any number of holes 241 and trim markers (e.g., trim markers are shown between the holes) having any of the characteristics of the holes 140, 142, 144, 146, 148, 149 and trim markers 150, 152 described with respect to the example augments 100 of FIGS. 1A-1C. The second and third augments can also include any of the features of the first augment 200A, also shown in FIG. 2A.

The augment 200A will now be described in further detail with respect to the close-up view of FIG. 2B. As previously described, the body of augment 200A can extend from the first end portion 230A to the second end portion 232A and can be formed as a buttress type augment. The augment can include a base 270 at the first end portion 230A that is adapted to be fastened to the shell 90, for example at shell holes 98. Extending away from the base 270 towards the second end portion 232A can be a plurality of extensions, such as a first extension 272 and a second extension 274. The first extension 272 can extend away from the base 270 in a first direction 235 and the second extension 274 can extend away from the base in a second direction 237.

The augment 200A of FIG. 2B can be described as including, but is not limited to, an augment having a generally V-shaped double extension, the V-shaped double extension being formed of the base 270, the first extension 272 and the second extension 274. The augment 200A is not limited to a V-shape, and other shapes including a U-shaped, Y-shaped or irregular shaped body, or any other suitable shaped body for supporting a shell can be provided.

In some examples and as shown in FIG. 2B, the first extension 272 can include a first hole 240 and a second hole 242 separated by a first extension first trim marker 250. The second extension 274 can include a third hole 244 and a fourth hole 246 separated by a second extension first trim marker 252.

In the example shown in FIG. 2B, the first extension 272 can include two trim markers: the first extension first trim marker 250, and a first extension second trim marker 254 that separates the second hole 242 from a fifth hole 248. Likewise, the second extension 274 can include: the second extension first trim marker 252, and a second extension second trim marker 256 that separates the fourth hole 246 from a sixth hole 249.

In some examples, each of the first and second extensions 272, 274 can each include a single trim marker. In some examples, only one of the first or second extension 272, 274 can include a trim marker. Or, one of the first or second extensions 272, 274 can include a plurality of trim markers. Various examples can include any suitable number of trim markers, holes and extensions in order to support the shell as needed depending on the particular application.

Figure 3:
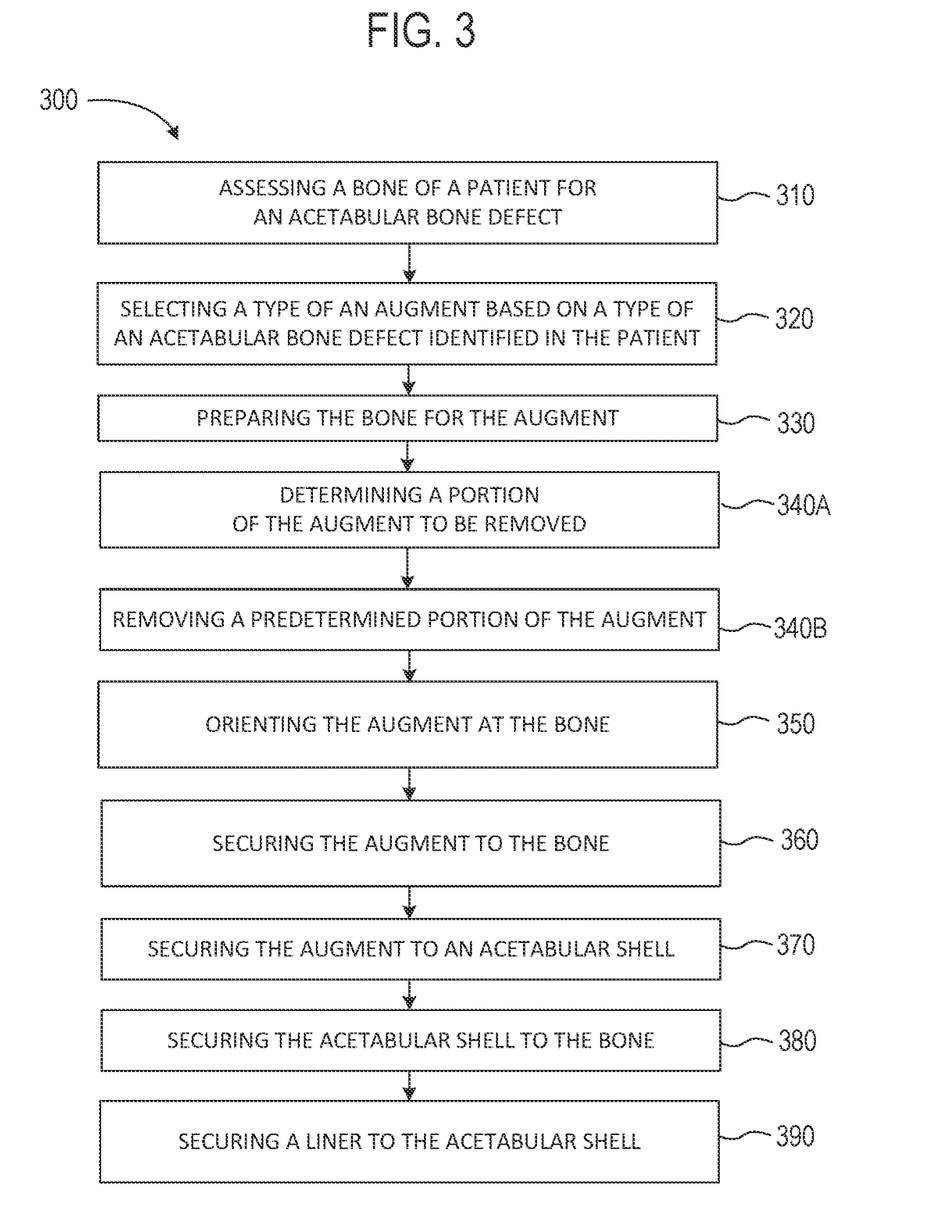
FIG. 3 is a flow chart illustrating a method of using augments to secure an acetabular shell to a bone of a patient, in accordance with at least one illustrative example.

FIG. 3 is a flow chart illustrating a method of using augments to secure an acetabular shell to a bone of a patient for a total hip arthroplasty, such as the augments of FIGS. 1A-1D and FIGS. 2A-2B, in accordance with at least one illustrative example.

Step 310 can include assessing a bone of a patient for an acetabular bone defect and identifying the type of acetabular bone defect. Based on the type of acetabular bone defect identified in the patient, step 320 can include selecting a type of an augment, such as the augments described above with respect to FIGS. 1A-1D and 2A-2B, to address the type of acetabular bone defect that was identified in the patient.

Step 330 can include preparing the bone for the augment. This can include reaming the acetabulum to prepare it to receive a shell or cup of the hip prosthesis.

Step 340A can include determining a portion of the augment to be removed. The portion of the augment to be removed can be a predetermined portion in the sense that, one or more removable portions are predetermined and are marked with trim markers identifying where the predetermined portions or trim locations are located, as previously described with reference to the examples of FIGS. 1A-1D and 2A-2B. Once the predetermined portion to be removed is determined, step 340B can include removing the predetermined portion of the augment.

As previously described with respect to the example augments of FIGS. 1A-1D and 2A-2B, in some examples of step 340B, the removing step can include removing a predetermined portion of the augment that extends between, for example, a trim marker (e.g., a first trim marker) and a second end portion of the augment. In some examples of step 340B, the removing step can include removing a predetermined portion of the augment that extends between a second trim marker and the second end portion.

Various methods and processes can be used to remove the predetermined portion. In some examples, where the augment can be formed partly or completely of a porous material that promotes boney ingrowth, the removal step can be complicated by this material. The voids in the porous material, the complicated 3-dimesional shapes, and the hardness, brittleness, fragility or other material characteristics of the augments can require methods of removal tailored to the particular augment to be modified.

Processes for removal of the predetermined portion and smoothing of edges following removal can include the use of: saws, dremmels, grinders, burnishers, sanders, chisels, plate benders and the like. Other methods of removing the predetermined portion and smoothing surfaces can include grinding, polishing, blasting, melting processes and chemical etching, or any other suitable smoothing process appropriate for the material, shape and porosity of the augment. In some examples, methods and tools that can apply a consistent force to break off the predetermined portion by applying a consistent force may be used. In some examples, such as the example augment 200A of FIG. 2B, step 340B can include removing more than one predetermined portion of the augment. For example, in the example of the augment 200A of FIG. 2B, the augment 200A has multiple extensions 272, 274 each having multiple trim markers 250, 252, 254, 256. In such an example a predetermined portion can be removed from the first extension 272 but not the second extension 274, from the second extension 274 but not the first extension 272, or from both the first and second extensions 272, 274.

Step 350 can include orienting the remaining body of the augment at the bone. Examples of locations where the augment can be oriented on the bone can include: a superior position on an ilium of the bone, or an inferior position on an ischium or ramus of the bone. Any other suitable location for an augment can also be used.

Step 360 can include securing the augment to the bone, such as by screws inserted through holes in the augment. In order for the augment to provide support for the shell, step 370 can include securing the augment to an acetabular shell by any of the methods described with respect to FIGS. 1A-1C and 2A-2B. For example, the augment can be secured to the shell by cement or screw attachment. Step 380 can include securing the acetabular shell to the bone, for example, by a fastener such as a screw. If using a liner, step 390 can include securing a liner to the acetabular shell, such as by cemented attachment or snap fit.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

VARIOUS NOTES AND EXAMPLES

To better illustrate the devices and methods disclosed herein, a non-limiting list of embodiments is provided herein.

Example 1 is an augment for supporting an acetabular shell at a bone, the augment comprising: a body having a first surface and a second surface opposite the first surface, the body extending from a first end portion to a second end portion, wherein the first end portion is adapted to be fixed to the acetabular shell, and wherein the body comprises a porous material that promotes boney ingrowth; a first hole and a second hole, each of the first and second holes extending through the body from the first surface to the second surface; and a trim marker located in between the first hole and the second hole.

In Example 2, the subject matter of Example 1 optionally includes wherein the trim marker indicates a location on the body that is more frangible than other portions of the body.

In Example 3, the subject matter of any one or more of Examples 1-2 optionally include wherein the augment is a buttress augment.

In Example 4, the subject matter of any one or more of Examples 1-3 optionally include wherein the body is adapted to structurally support the acetabular shell in a patient having a Paprosky type IIIA defect.

In Example 5, the subject matter of any one or more of Examples 1-4 optionally include a third hole and a fourth hole, each of the third and fourth holes extending through the body from the first surface to the second surface, and wherein the trim marker is located in between the third hole and the fourth hole.

In Example 6, the subject matter of Example 5 optionally includes the body comprising a first portion including the first hole and the third hole, and a second portion including the second hole and the fourth hole, wherein the trim marker is located in between the first portion and the second portion, and wherein a thickness of the body from the first surface to the second surface at the trim marker is less than the thickness of at least a portion of the first and second portions adjacent to the trim marker.

In Example 7, the subject matter of any one or more of Examples 1-6 optionally include wherein the first surface comprises a smooth surface, and wherein the second surface comprises the porous material that promotes boney ingrowth.

In Example 8, the subject matter of any one or more of Examples 1-7 optionally include wherein the first surface has a first coefficient of friction, and wherein the second surface has a second coefficient of friction, and wherein the first coefficient of friction is less than the second coefficient of friction.

In Example 9, the subject matter of any one or more of Examples 1-8 optionally include wherein the first end portion includes a third surface that is shaped to conform to an exterior surface of the acetabular shell.

In Example 10, the subject matter of any one or more of Examples 1-9 optionally include wherein the augment is a buttress augment and the first end portion has a curved surface that is shaped to conform to a generally spherical surface portion of the acetabular shell.

In Example 11, the subject matter of any one or more of Examples 1-10 optionally include the body comprising a base at the first end portion, a first extension extending away from the base in a first direction, and a second extension extending away from the base in a second direction, wherein the first and second holes and the trim marker are on the first extension, and wherein a third hole, a fourth hole and a second extension trim marker are on the second extension.

Example 12 is a buttress augment for supporting an acetabular shell at a bone, the buttress augment comprising: a body having a first surface and a second surface opposite the first surface, the body extending from a first end portion to a second end portion, wherein the first end portion is adapted to be fixed to the acetabular shell a first hole and a second hole, each of the first and second holes extending through the body from the first surface to the second surface; and a trim marker located in between the first hole and the second hole.

In Example 13, the subject matter of Example 12 optionally includes wherein the body comprises a porous material that promotes boney ingrowth.

In Example 14, the subject matter of any one or more of Examples 12-13 optionally include wherein the first surface comprises a smooth surface, and wherein the second surface comprises a porous material that promotes boney ingrowth.

In Example 15, the subject matter of any one or more of Examples 12-14 optionally include wherein the trim marker indicates a location on the body that is more frangible than adjacent portions of the body.

Example 16 is a method for securing an acetabular shell to a bone of a patient, the method comprising: assessing the patient for an acetabular bone defect and identifying a type of acetabular bone defect; selecting a type of an augment based on the type of the acetabular bone defect identified in the patient, the augment having: a body formed of a porous material that promotes boney ingrowth, the body having a first surface and a second surface opposite the first surface, the body extending from a first end portion to a second end portion, wherein the first end portion is adapted to be fixed to the acetabular shell, the body further including a trim marker indicating a trim location; removing a predetermined portion of the augment; orienting the augment at the bone; securing the augment to the bone; securing the augment to the acetabular shell; and securing the acetabular shell to the bone.

In Example 17, the subject matter of Example 16 optionally includes wherein the trim marker indicates a location on the body that is more frangible than other portions of the body.

In Example 18, the subject matter of any one or more of Examples 16-17 optionally include wherein the augment is a buttress augment, and wherein removing the predetermined portion of the augment includes removing at least a first portion of the augment extending from the trim marker to the second end portion.

In Example 19, the subject matter of any one or more of Examples 16-18 optionally include the augment further comprising a first hole and a second hole, each of the first and second holes extending through the body from the first surface to the second surface.

In Example 20, the subject matter of any one or more of Examples 16-19 optionally include wherein removing the predetermined portion of the augment includes removing a second portion that extends between a second trim marker and the second end portion, wherein the second trim marker indicates a second trim location, and wherein the second portion includes the porous material that promotes boney ingrowth.

In Example 21, the subject matter of any one or more of Examples 16-20 optionally include wherein orienting the augment at the bone includes orienting the augment at a superior position on an ilium of the bone.

In Example 22, the subject matter of any one or more of Examples 16-21 optionally include wherein orienting the augment at the bone includes orienting the augment at an inferior position on an ischium or ramus of the bone.

In Example 23, the subject matter of any one or more of Examples 16-22 optionally include wherein the body comprises a base at the first end portion, a first extension extending away from the base in a first direction, and a second extension extending away from the base in a second direction, wherein the first and second holes and the trim marker are located on the first extension, and wherein a third hole, a fourth hole and a second extension trim marker are located on the second extension.

In Example 24, the subject matter of Example 23 optionally includes wherein removing the predetermined portion of the augment includes removing at least one of: the body extending from the trim marker to the second end portion, and the body extending from the second extension trim marker to the second end portion.

What is claimed is:

1. An augment for supporting an implant at a bone and for attaching the implant to the bone of a patient, the augment comprising:
a body having a first surface and a second surface opposite the first surface, the body extending along a longitudinal axis from a first end portion to a second end portion and defining a longitudinal body length therebetween, wherein the first end portion is adapted to be fixed to the implant, and the first end portion has a concave third surface that intersects the first surface at a first end of the third surface and the second surface at a second end of the third surface and is shaped to conform to an exterior surface of the implant, and wherein the body comprises a porous material that promotes boney ingrowth such that the second surface comprises the porous material that promotes boney ingrowth and the first surface comprises a smooth surface;

a first hole and a second hole, each of the first and second holes extending through the body from the first surface to the second surface; and a trim marker located in between the first hole and the second hole, wherein the trim marker indicates a location on the body to cut through the porous material and the smooth surface to separate the second end portion of the augment in order to reduce the longitudinal body length of the augment.

2. The augment of claim 1, wherein the trim marker indicates a location on the body that is more frangible than other portions of the body.

3. The augment of claim 1, wherein the augment is a buttress augment.

4. The augment of claim 1, wherein the body is adapted to structurally support the implant in a patient having a Paprosky type IIIA defect.

5. The augment of claim 1, further comprising a third hole and a fourth hole, each of the third and fourth holes extending through the body from the first surface to the second surface, and wherein the trim marker is located in between the third hole and the fourth hole.

6. The augment of claim 5, the body comprising a first portion including the first hole and the third hole, and a second portion including the second hole and the fourth hole, wherein the trim marker is located in between the first portion and the second portion, and wherein a thickness of the body from the first surface to the second surface at the trim marker is less than the thickness of at least a portion of the first and second portions adjacent to the trim marker.

7. The augment of claim 1, wherein the first surface has a first coefficient of friction, and wherein the second surface has a second coefficient of friction, and wherein the first coefficient of friction is less than the second coefficient of friction.

8. The augment of claim 1, wherein the implant is an acetabular shell and the third surface of the first end portion is shaped to conform to the exterior surface of the acetabular shell.

9. The augment of claim 1, wherein the augment is a buttress augment and the implant is an acetabular shell such that the first end portion has a curved surface that is shaped to conform to a generally spherical surface portion of the acetabular shell.

10. The augment of claim 1, the body comprising a base at the first end portion, a first extension extending away from the base in a first direction, and a second extension extending away from the base in a second direction, wherein the first and second holes and the trim marker are on the first extension, and wherein a third hole, a fourth hole and a second extension trim marker are on the second extension.

11. A buttress augment for supporting an acetabular shell at a bone, the buttress augment comprising:

a body having a first surface and a second surface opposite the first surface, the body extending along a longitudinal axis from a first end portion to a second end portion and defining a longitudinal body length therebetween, wherein the first end portion is adapted to be fixed to the acetabular shell, and the first end portion has a concave third surface that extends from the first surface to the second surface, faces in a direction different from the first surface and the second surface, and is shaped to conform to an exterior surface of the acetabular shell, wherein the second surface comprises a porous material that promotes boney ingrowth and the first surface comprises a smooth surface;

a first hole and a second hole, each of the first and second holes extending through the body from the first surface to the second surface; and a trim marker located in between the first hole and the second hole, wherein the trim marker indicates a location on the body to separate the second end portion of the augment in order to reduce the longitudinal body length of the augment.

12. The buttress augment of claim 11, wherein the body comprises the porous material that promotes boney ingrowth.

13. The buttress augment of claim 11, wherein the trim marker indicates a location on the body that is more frangible than adjacent portions of the body.

14. An augment for supporting an implant at a bone and for attaching the implant to the bone of a patient, the augment comprising:

a body having a first surface and a second surface opposite the first surface, the body extending along a longitudinal axis from a first end portion to a second end portion, wherein:

the body has a longitudinal length defined between the first end portion and the second end portion;

the first end portion is adapted to be fixed to the implant, the first end portion having a concave third surface that extends between the first surface and the second surface and is shaped to conform to an exterior surface of the implant; and the body comprises a porous material that promotes boney ingrowth such that the first surface comprises a smooth surface and the second surface comprises the porous material that promotes boney ingrowth;

a first hole and a second hole, each of the first and second holes extending through the body from the first surface to the second surface; and a trim marker located in between the first hole and the second hole;

wherein the trim marker indicates a location on the body to cut through the porous material and the smooth surface to separate the second end portion of the augment;

wherein the trim marker includes a first recess in the first surface and a second recess in the second surface, the second recess aligned with the first recess; and wherein separating the second end portion reduces the longitudinal length of the body.

15. The augment of claim 14, wherein the trim marker indicates a location on the body that is more frangible than other portions of the body.

16. The augment of claim 14, wherein the augment is a buttress augment and the implant is an acetabular shell, wherein the first end portion has a curved surface that is shaped to conform to a generally spherical surface portion of the acetabular shell.

17. The augment of claim 14, wherein a thickness of the body from the first surface to the second surface at the trim marker is less than the thickness of at least a portion of the first and second portions adjacent to the trim marker.

* * * * *